United States Patent [19]

Hayes et al.

[11] Patent Number: 5,364,383
[45] Date of Patent: Nov. 15, 1994

[54] TAMPON

[75] Inventors: Harry Hayes, Wilbraham, Mass.; Charlotte C. Wakeham, Hayling Island, England

[73] Assignee: Tambrands, Inc., White Plains, N.Y.

[21] Appl. No.: 37,254

[22] Filed: Mar. 26, 1993

[51] Int. Cl.⁵ .................... A61F 13/15; A61F 13/20
[52] U.S. Cl. ........................... 604/384; 604/358; 604/374; 604/378; 604/385.1; 604/904
[58] Field of Search ............. 604/358, 367, 374–380, 604/384, 385.1, 904

[56] References Cited

U.S. PATENT DOCUMENTS

| | | | |
|---|---|---|---|
| 1,941,717 | 1/1934 | Rabell | 604/385.1 |
| 1,964,911 | 7/1934 | Haas . | |
| 2,444,528 | 7/1948 | Popper et al. . | |
| 2,464,310 | 3/1949 | Harwood . | |
| 2,761,449 | 9/1956 | Bletzinger . | |
| 2,926,394 | 3/1960 | Bletzinger et al. | 604/375 |
| 2,934,068 | 4/1960 | Graham, Jr. et al. . | |
| 3,013,558 | 12/1961 | Leupold . | |
| 3,057,037 | 10/1962 | Carney et al. | 604/375 |
| 3,063,453 | 11/1962 | Brecht . | |
| 3,177,872 | 4/1965 | Pearman . | |
| 3,320,956 | 5/1967 | Steiger . | |
| 3,593,715 | 7/1971 | Merrill . | |
| 3,709,221 | 1/1973 | Riely | 602/43 |
| 4,289,824 | 9/1981 | Smith | 604/904 |
| 4,973,503 | 11/1990 | Hotchkiss . | |
| 5,149,332 | 9/1992 | Walton et al. . | |
| 5,171,235 | 12/1992 | Theis et al. . | |

FOREIGN PATENT DOCUMENTS

| | | | |
|---|---|---|---|
| WO89/06524 | 1/1988 | Japan . | |
| 2094637A | 9/1982 | United Kingdom . | |
| 8901062 | 2/1989 | WIPO | 604/367 |

OTHER PUBLICATIONS

Cellulose—Ency. of Chem. Tech., John Wiley & Sons, 3rd Ed. 1982, vol. 5, pp. 70–114.
Rayon—Ency. of Chem. Tech., John Wiley & Sons, 3rd Ed. 1982, vol. 19, pp. 855–879.

Primary Examiner—Randall L. Green
Assistant Examiner—P. Zuttarelli
Attorney, Agent, or Firm—Fish & Richardson

[57] ABSTRACT

A tampon comprising a compressed pledget of absorbent material, shaped for insertion into a body cavity, and a withdrawal cord attached to the tampon to facilitate removal of the tampon from the body cavity. The pledget, prior to compression, is a filament tow of substantially hydrophilic filaments. The filaments have a substantially permanently crimped configuration, and are disposed in a randomly out-of-phase orientation with respect to each other so as to increase the pore volume ratio of the pledget, i.e., the fraction of pledget volume occupied by interfilament spaces or interstices between filaments. Preferably the pore volume ratio of the tampon is in the range of 60 to 95%, more preferably 70 to 90%, most preferably 80 to 85%.

34 Claims, 4 Drawing Sheets

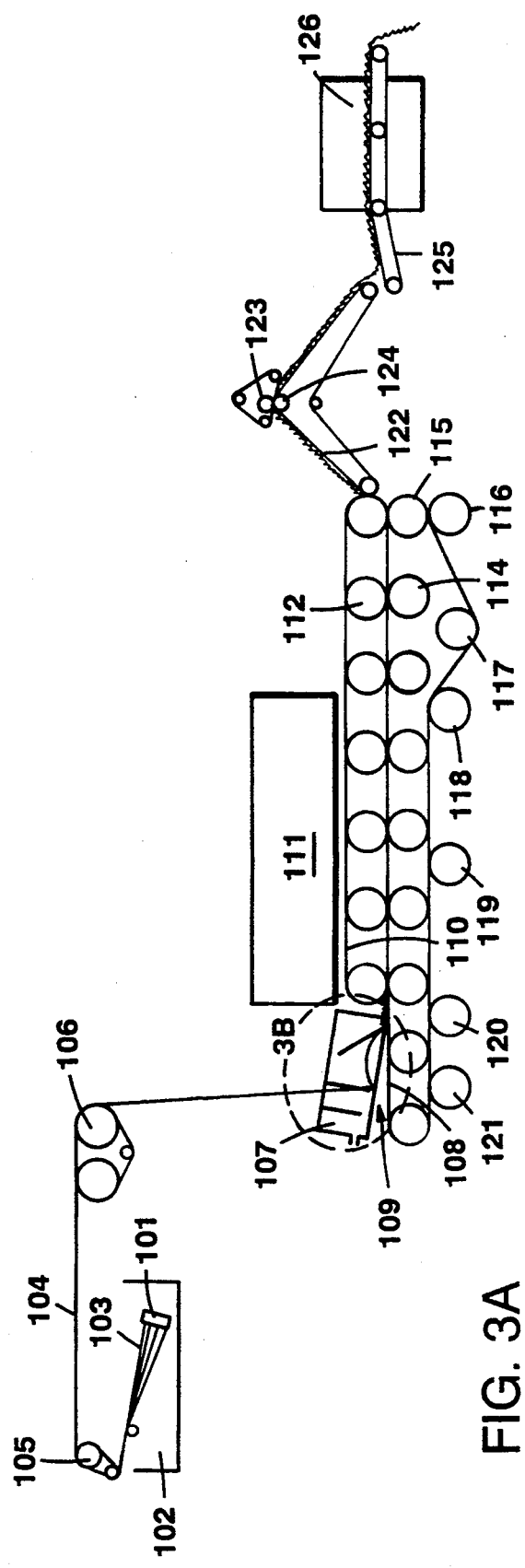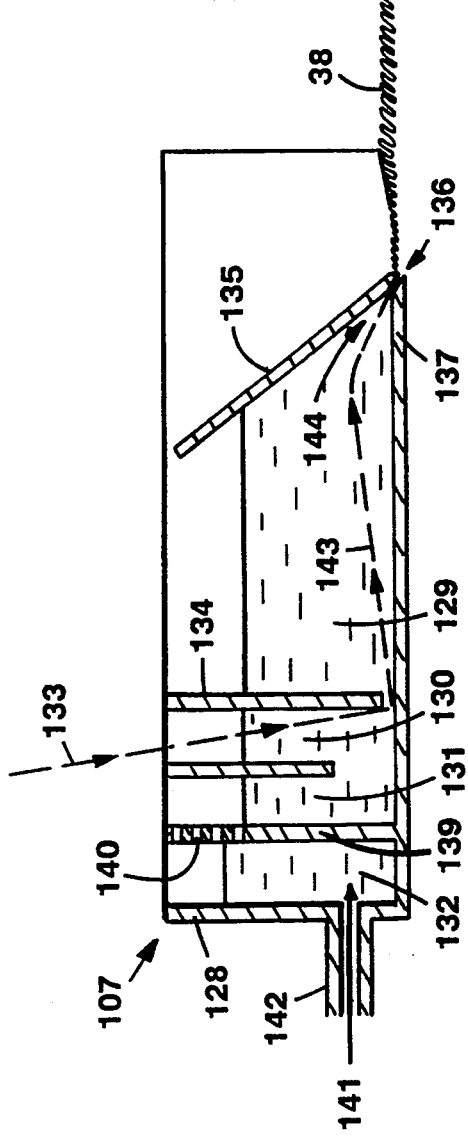
FIG. 3A
FIG. 3B

TAMPON

BACKGROUND OF THE INVENTION

The invention relates to tampons, including catamenial tampons.

Tampons are typically manufactured by cutting an absorbent material into a desired length, forming the length of material into a pledget, and compressing the pledget.

A long standing problem with tampons has been their tendency to leak prematurely, i.e., prior to full saturation with menstrual fluid, due to local conditions of oversaturation and undersaturation in the absorbent material.

The absorbency of a tampon at full saturation is determined, in major part, by the fiber weight which is used in the tampon. Increasing the fiber weight will increase absorbency, but will also deleteriously increase the cost and size of the tampon. Increasing absorbency is generally not a cure for premature leakage; it typically increases the total absorption at leakage, but does not avoid leakage prior to full saturation.

Conventional tampons are typically manufactured using absorbent material comprised of short fibers provided in the form of a nonwoven web. These nonwoven materials can be prone to "fiber fluff off", i.e., detachment of the short fibers from the tampon during use or removal of the tampon.

Another known tampon construction, which in the past has sometimes been proposed as a solution to fiber fluff off, is a bundle of continuous long filaments, i.e., a "filament tow". Such tampons are described in, e.g., U.S. Pat. Nos. 3,177,872, 3,320,956, and 2,934,068.

SUMMARY OF THE INVENTION

The invention features an improved tampon, with excellent absorbency and resistance to premature leakage. Advantageously, the improvement in absorbency is achieved using significantly lower fiber weights than in conventional tampons, thus reducing manufacturing costs.

The tampon includes a compressed pledget of absorbent material, shaped for insertion into a body cavity, and a withdrawal cord attached to the tampon to facilitate removal of the tampon from the body cavity. The pledget, prior to compression, includes an absorbent material derived from a filament tow of substantially hydrophilic filaments. The filaments have a substantially permanently crimped configuration, and are disposed in a randomly out-of-phase orientation with respect to each other so as to increase the pore volume ratio, i.e., the fraction of volume occupied by interfilament spaces or interstices between filaments, of the pledget. Preferably the pore volume ratio of the compressed tampon is in the range of 60 to 95%, more preferably 70 to 90%, and most preferably 80 to 85%.

By "compressed", it is meant that the pledget is compressed to an extent such that it does not exhibit a significant amount of expansion during storage at ambient conditions, i.e., room temperature, atmospheric pressure and 50% relative humidity. Preferably, the pledget is compressed sufficiently to prevent it from expanding more than 65% of its initial compressed volume over 48 hours under ambient conditions. This degree of compression is typically achieved by compressing the pledget to a bulk density of at least 0.05 g/cc, more preferably from about 0.1 to 0.6 g/cc, most preferably 0.2 to 0.4 g/cc.

By "substantially hydrophilic", it is meant that the filaments are readily wet by aqueous liquids, e.g., menstrual fluid. The hydrophilicity of the filaments is determined by the number of available hydroxyl groups present on the surface of the material. It is preferred that the filaments contain at least two available hydroxyl groups per monomer, more at least preferably three. Cellulosic materials have either one (cellulose diacetate), two (cellulose acetate), or three (viscose) hydroxyl groups, and thus viscose is preferred.

By "substantially permanently crimped configuration", it is meant that the individual filaments have a random sinuous configuration. The filaments are given this sinuous configuration in a manner which imparts a rigidity to the crimp, i.e., prevents the crimp from being readily removed by pulling or wetting of the filament or filament tow. The permanence of the crimp is defined by its substantial recovery after extension to but not beyond the elastic limit of the crimp of the individual filaments.

By "randomly out-of-phase", it is meant that the sinuous configuration of individual crimped filaments is randomly out of phase with respect to that of neighboring filaments, i.e., that the peaks and valleys of the filaments are randomly misaligned, with resulting increase in the volume of interfilament spaces (i.e., the pore volume).

The term "pore volume ratio" as used herein refers to the fraction of space within a structure (e.g., the uncompressed pledget or the compressed tampon) that comprises the interfilament spaces or interstices. The ratio is calculated as a percentage by the following formula:

$$\frac{\text{total volume} - \text{volume of filaments}}{\text{total volume}} \times 100$$

Preferably, the pore volume ratio of the uncompressed pledget is greater than 95%, more preferably greater than 96%. The pore volume ratio of the compressed tampon is lower, most preferably in the range of 80 to 85%.

In some preferred embodiments, the degree of the out of phase relationship between filaments is increased prior to incorporation of the absorbent material into the pledget by blooming the filament tow, preferably by pulling it along its longitudinal dimension and then allowing it to relax. The pulling is enough to separate the individual crimped filaments into a more out of phase relationship, but not so much as to exceed the elastic limit of the crimp (and thereby remove the crimp). The absorbency of the finished tampon is typically directly related to the degree to which the filament web is bloomed. Accordingly, tampons of different absorbencies can be formed using a single type of absorbent material, by varying the degree to which the web is bloomed.

In some preferred embodiments, the filament tow comprises continuous viscose filaments, and both the permanence of the crimped configurations and the out of phase relationships of the filaments are imparted by overfeeding during regeneration of the viscose. Preferred viscose filaments can have a decitex in the range of 0.5 to 5, more preferably 0.5 to 10 and most preferably 0.5 to 20 decitex.

In a preferred embodiment, the absorbent material comprises a continuous filament tow of regenerated viscose cellulose filaments. The tow is formed by a process in which a running tow in a flowing liquid in the form of a spread band is overfed onto a moving foraminous support to separate it from the liquid, so as to form a coherent web, which web is dried. During formation of the continuous filament tow of cellulosic viscose filaments, the filaments are in the partially regenerated state and the flowing liquid is acidic so that regeneration of the partially regenerated viscose occurs prior to, during, and after the filament tow is overfed onto the moving foraminous support. Preferably, the dried web is then stretched back into tow form. More preferably, the process is carried out by passing the tow through a spreader box and impacting the spread band upon the foraminous support through a wedgeshaped channel. The foraminous support may be moved at a speed at least two times, usually in the range 5 to 40 times, slower than the rate of feed of the band onto the foraminous support, preferably 15 to 25 times slower. The band formed on the foraminous support may be washed by means of conventional wash liquor, and dried partially by passage through the nip of a mangle prior to complete drying in any suitable drying machine such as a drum drier or through air dryer.

In some preferred embodiments, the filaments are, themselves, absorbent, meaning the filaments have internal interstices capable of absorbing and retaining fluid. Alternatively, the filaments can be spun with hydrocolloid inclusions of polymers to enhance the intrafilament liquid retention. One measure of the absorption characteristics of the filaments is water imbibition value, which is calculated by the following formula:

$$\frac{\text{weight of wet filaments} - \text{weight of dry filaments}}{\text{weight of dry filaments}}$$

multiplied by 100 to obtain a percentage value. Preferably, the filaments have a water imbibition value of at least 40%, more preferably at least 90%. Preferred filaments are cellulosic filaments, more preferably viscose.

In another aspect, the invention features manufacturing a tampon by a method comprising the steps of: a) regenerating a plurality of continuous filaments of viscose rayon in an acid bath; b) before the regeneration is complete, feeding the filaments into a spreader box under liquid at a first speed; c) providing a restriction within the spreader box so that the filaments exit the spreader box at a second speed substantially lower than the first speed, causing the filaments to form an overfed tow web wherein the filaments have a substantially permanently crimped configuration; d) after regeneration is complete, blooming the overfed web to increase the pore volume ratio of the web; e) forming a pledget from a portion of the web; and f) compressing the pledget to form a compressed tampon.

In preferred embodiments, a dam is provided in the spreader box which is inclined at an acute angle to the base of the box (e.g., in the range 30 to 60° preferably 40 to 50°). The spreader box is preferably two to twenty times the width of the running tow fed to it, and the base of the spreader box is preferably disposed at an angle in the range 3° to 10° to the horizontal. The spreader box preferably includes a baffle beneath which the tow is passed prior to ballooning upward, outward and downward and passing out through a elongate slit at the downstream edge of the box.

Other features of the invention will be apparent from the following description of preferred embodiments, and from the claims.

BRIEF DESCRIPTION OF THE DRAWINGS

FIGS. 3a-3g schematically illustrate a process for manufacturing a tampon according to one embodiment of the invention.

DESCRIPTION OF THE PREFERRED EMBODIMENTS

Figure 1:
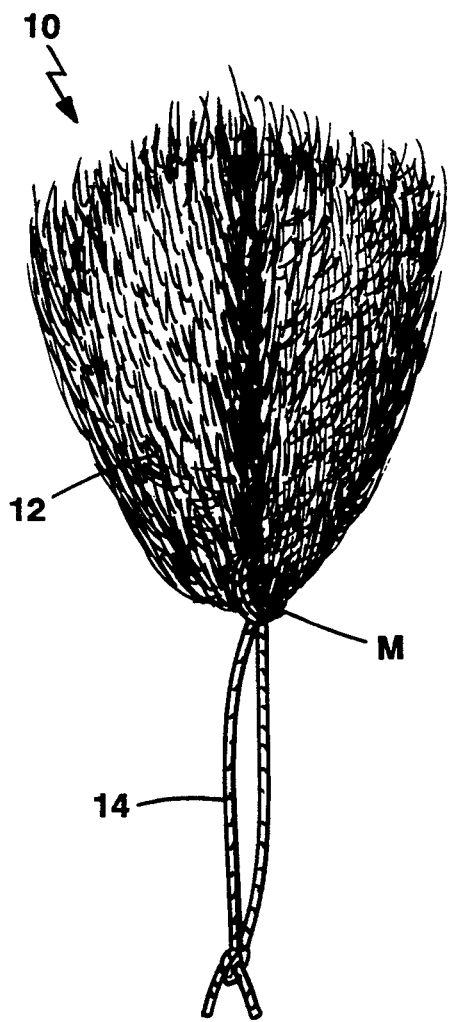
FIG. 1 is side view of an uncompressed pledget according to one embodiment of the invention.
Figure 2:
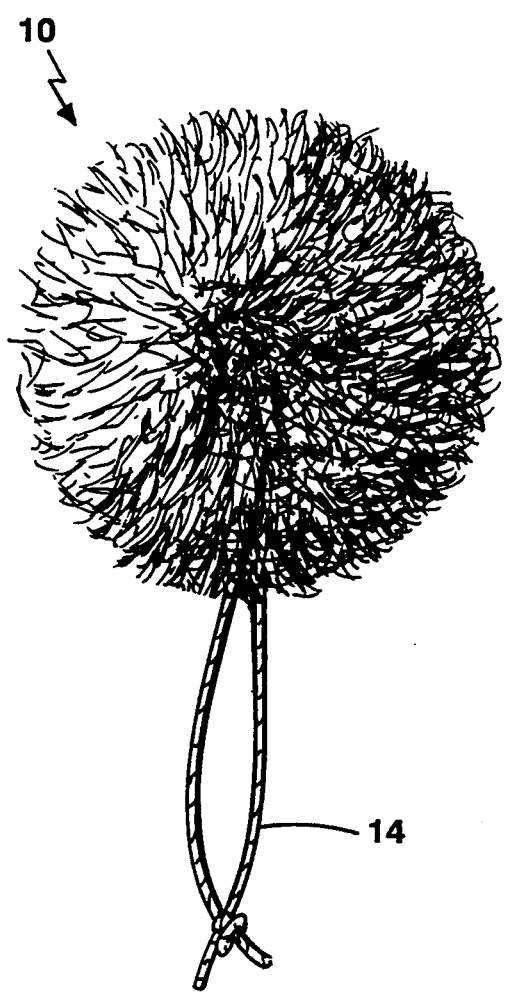
FIG. 2 is a side view of an uncompressed pledget according to another embodiment of the invention.

Two preferred pledget configurations are shown in FIGS. 1 and 2 (other configurations are possible). Pledget 10 of FIG. 1, which is most preferred, comprises a length of absorbent material 12, folded in half about a withdrawal cord 14 attached at its approximate midpoint M. In the alternate embodiment shown in FIG. 2, the filament tow is fluffed around the withdrawal cord, forming a "pom-pom". To form the finished tampon, shown in FIG. 3g, the pledget is compressed substantially radially.

The absorbent material used to form the pledget may be any material which is sufficiently hydrophilic in surface character and absorbent to provide adequate absorption of menstrual fluids when used in a tampon constructed according to the invention. Preferably, the material has a water imbibition value of at least 40%, more preferably at least 90%, and contains at least two, more preferably at least three, available hydroxyl groups per monomer. Absorption tends to be more dependent on hydrophilicity (which affects water storage between filaments) than on absorptivity (which affects water storage within filaments), and thus nonabsorptive filaments can be used as long as they are sufficiently hydrophilic.

It is also preferred that the filaments be formed of a material in which a substantially permanent crimp can be set. The crimp can be achieved in several ways, e.g., by overfeeding into a spreader box (or stuffer box) during cellulose regeneration, by heat setting, by chemical means, or by mechanical means (e.g., by using known compressive crimping processes such as Sanforising TM, Micrex TM, or Clupak TM, in which a tow is overfed into a space formed between two rollers and a feed shoe, causing the tow to buckle, or by processing the filaments through gear elements). What is important is that the crimp be substantially permanent so that it is difficult to remove from the filaments during processing.

A particularly preferred filament material is viscose. Viscose has three available hydroxyl groups per monomer, and has a water imbibition value of about 95 to 280%. Viscose can be permanently crimped during regeneration, as described below with reference to FIGS. 3a-3g, or by chemical means.

Other materials, e.g., synthetic, thermoplastic filaments and other cellulosic filaments (e.g., cellulose acetate), could be used if they are processed (e.g., by being given a surface treatment) so as to be substantially hydrophilic. Thermoplastic synthetic filaments and cellulosic filaments such as cellulose acetate can successfully be crimped by heat set and mechanical techniques. Super-inflated filaments can be used, i.e., hollow filaments spun to include a lumen, as described in British Patent Application No. 2,022,505.

FIGS. 3a–3g illustrate a preferred manufacturing process. A preferred process for forming the tow web is described below with reference to FIGS. 3a to 3b.

As is well known, viscose cellulose filaments are produced by spinning viscose dope in the form of a solution of sodium cellulose xanthate having a cellulose content in the range 5 to 12% by weight and a caustic soda content of 4 to 10% preferably 5 to 7% by weight into an acidic regeneration bath, typically containing 7 to 10% sulphuric acid, 10 to 28% sodium sulphate, and 0 to 4%, more specifically 0.5 to 1.5%, zinc sulphate in a bath at 30° to 70° C., more specifically 45° to 60° C., so as to neutralize the alkali and to coagulate and regenerate the cellulose to form cellulosic filaments. The viscose dope may have a full range of salt figures, although 4 to 12 are preferred. Regeneration occurs from the surface of the filaments, where a skin of cellulose is initially formed, through into the interior of the filaments.

The viscose cellulose filaments may be produced in a conventional manner by the extrusion or spinning of a viscose dope through a spinnerette into an acid bath. The viscose filaments may be of a conventional round cross-section, or may be of a trilobal, Y-shaped, L-shaped or any other suitable cross-sectional shape. The filaments may be simple viscose filaments or may contain additives such as a matting agent, e.g., $TiO_2$ or an absorbent enhancing material such as carboxymethyl cellulose or any other suitable additive. The viscose dope may contain polyethylene glycol or other known additives and modifiers such as polyalcohols, soluble dithiocarbonates, soluble aliphatic and alicyclic amines, oxyethanols and quinoline.

Referring to FIG. 3a, the overall tow-web processing system is shown. Dope is extruded through a spinnerette 100 into a spin bath 102 so as to form a plurality of elongate members 103. The viscose dope has a salt figure in the range 5.5 to 6.5 and contains 4% polyethylene glycol (PEG) having a molecular weight of 1,450. The spin bath 102 contains an aqueous solution of sulphuric acid, zinc sulphate, and sodium sulphate. Typically, the spin bath acid can be in the range 7 to 9.75%, there would be about 1% zinc in the spin bath, based on zinc sulphate, and 22 to 25% sodium sulphate.

On emerging from the spinnerette 100, the viscose solution immediately coagulates and forms a cuticle or exterior layer of cellulose around each emerging elongate member. Coagulation and regeneration of the cellulose then occurs as a diffusion-controlled process with diffusion of acid into the elongate members causing regeneration of the cellulose and liberation of carbon disulphide.

Regeneration does not occur immediately, but takes a finite period of time. The regeneration of the elongate members to form cellulose filaments occurs throughout a significant portion of subsequent processing after emerging from the spinning bath 102 and during washing. Regeneration is occurring as long as $CS_2$ is being released by the filaments, as regeneration is not complete until all the cellulose xanthic acid in a filament has decomposed to form cellulose and $CS_2$ and all the $CS_2$ has been liberated.

The elongate members 103, now considered to be in the form of filaments, are gathered together as a continuous tow 104 which is passed over rollers 105, 106 and passed in an untangled manner into a spreader box 107.

Emerging from the downstream end of the spreader box 107, the continuous tow is overfed onto a continuous mesh belt 108 which is moving in the direction of arrow 109. The tow 104 is produced at a spinning speed of 15 meters per minute and the belt 108 is moved at a speed of 0.75 meters per minute. Thus, the tow is overfed onto the belt 108 at a ratio of about 30:1 to 5:1, more preferably about 20:1. The continuous filament tow is then trapped between the foraminous mesh belt 108 and an upper belt 110 which, initially, only loosely grips the tow web as it lies on the lower belt 108. The laid out tow web, referred to herein as a spread laid web, is still undergoing regeneration, with the formation of cellulose and the emission of carbon disulphide, as the tow is laid onto the foraminous mesh belt 108.

A series of washing heads are positioned within a washing machine 111 over the belt 110 to spray wash liquor (e.g. water) over the spread lain web to continue the regeneration and to wash out the acid and carbon disulphide from the web.

As the spread laid web approaches the downstream ends of the belts 108 and 110 it passes through a first nip created between rollers 112 and 114 and a smaller second nip created between rollers 113 and 115 to squeeze excess water from the spread laid web. It can be seen that the endless foraminous belt 108 has a return run which is controlled by a series of lower rollers 116 to 121. A finish or softener may be dripped onto the tow between rollers 112 and 113. Typical finishes include soap, PRG esters or glycerol or other suitable fibre finishes.

The spread laid tow is then passed along a further belt conveyor 122 up into the nip of a mangle 123, 124. The tow then passes down an inclined portion of the conveyor 122 and is laid onto a further endless belt 125 which passes through a drier 126.

FIG. 3b shows the spreader box 107 of FIG. 3a in more detail. The spreader box 107 essentially comprises a rectangular box 128 having a series of chambers 129, 130, 131, 132 built into the box. Tow 104 from the spin bath follows the dotted line 133 through the spreader box. The tow first enters chamber 130 and passes underneath a downwardly-directed baffle 134 to enter the chamber 129. Within the chamber 129, the tow moves upwardly and enters a region adjacent an inclined dam wall 135 to be forced through an exit aperture 136 formed between the dam wall 135 and a base 137 of the box 128.

The chamber 130 is in direct communication with a further chamber 131 via the underside of a further downwardly directed baffle 138. A yet further baffle 139 having apertures 140 in its upper portion separates chambers 131 and 132.

Acid liquor which is more dilute than that contained in the spin bath 102 (but still sufficiently acidic to continue the regeneration) is forced into the spreader box 128 through an aperture 141, via an inlet pipe 142.

The liquor thus flows through the spreader box via chambers 132, 131, 130 and 129 and leaves the spreader box via aperture 136. The restriction caused by the dam wall 135 and the small size of the exit aperture 136 tends to force the tow upwardly in its passage though chamber 129 to follow roughly along the line 143. This causes the tow to spread across the entire width of the spreader box and to go from a substantially compact almost circular tow in the region of portion 133 into a spread tow in the region 144 as it approaches the exit aperture 136. The angle of the obstruction, and the clearance between the obstruction and the box, will determine the amount of overfeed obtained. The spreader box causes the filaments to take on a crimped, overlapping sinuous configuration in a dense tow web. Because this step is performed during regeneration, the crimped configuration is "set" into the filaments, and is not readily removed. The angle of the dam wall 135 to the base 137 is shown as about 50°. The base 137 is inclined at some 6° to the horizontal.

Four sample tow webs were produced from viscose solutions having differing salt figures. These four samples were each spun through a spinnerette containing 17,388 Y-section holes to produce tow webs of individual filaments of decitex as set out in the tables below. In each case, the viscose contained 4% PEG 1450 based on the weight of cellulose in the viscose solution. The samples were spun at 15 meters per minute and the belt 8 was operated at 0.75 meters per minute.

The values for salt figure, spin bath acid, spin bath zinc, spin bath sulphate, spin bath flow, air stretch—stretching in the atmosphere between rollers 105 and 106, and hot stretch—stretching in a bath of spin liquor at a temperature of 96° C. were as set out in Table 1 below.

TABLE 1

Specification of Tow Web Samples.

| Sample No. | 1 | 2 | 3 | 4 |
|---|---|---|---|---|
| Salt Figure | 6.5 | 6.2 | 5.5 | 5.8 |
| % Spin Bath $H_2SO_4$ (w/w) | 9.28 | 9.26 | 9.35 | 9.52 |
| % Spin Bath $ZnSO_4$ (w/w) | 0.95 | 0.97 | 0.98 | 1.00 |
| % Spin Bath $Na_2SO_4$ (w/w) | 23.6 | 23.8 | 24.0 | 24.1 |
| Spin Bath Flow (1/min) | 50 | 50 | 50 | 65 |
| % Air Stretch | 7 | 7 | 7 | none |
| % Hot Stretch | none | none | none | 7 |

The air stretch may be in the range 0 to 30%, or 5 to 20%.

The physical properties of the tow web samples were then measured to give the information contained in Table 2 below.

TABLE 2

Physical Properties For Tow Web Samples.

| Sample No. | 1 | 2 | 3 | 4 |
|---|---|---|---|---|
| Decitex | 3.32 | 3.82 | 3.08 | 4.52 |
| % Extension | 30.25 | 41.01 | 31.81 | 41.53 |
| Tenacity (cN/tex) | 11.02 | 10.45 | 10.96 | 11.35 |
| Crimp Frequency (waves/cm) | 1.01 | 1.01 | 1.41 | 1.01 |
| Crimp Ratio | 2.83 | 2.23 | 2.39 | 2.81 |
| Crimp Amplitude (mm) | 2.83 | 2.22 | 1.65 | 2.31 |
| Crimp Energy (cN · cm) | 0.01410 | 0.013384 | 0.011099 | 0.009240 |
| Fabric Weight (g) | 650 | 650 | 650 | 650 |

The crimp obtained by the process shown in FIG. 3a can be characterized as "chemomechanical", i.e., having attributes of both chemical crimp (permanence) and mechanical crimp (high amplitude and regularity).

In a further series of tests, the overfeed ratio was varied while all other conditions and materials were kept the same. The results are given below.

TABLE 3

| Overfeed Ratio | Absorbency (g/g) |
|---|---|
| 10:1 | 4.2 |
| 15:1 | 4.4 |

TABLE 3-continued

| Overfeed Ratio | Absorbency (g/g) |
|---|---|
| 20:1 | 4.6 |

Further description of the web-forming process is found in U.K. Patent Document No. 1,387,566 (incorporated by reference).

Figure 3C:

Next, as shown in FIG. 3c, the filament tow is bloomed by pulling it longitudinally, and then allowing it to relax. The resulting filament tow has greatly increased pore volume. The blooming produces a randomly out-of-phase relationship between the sinuous, crimped filaments, so that peaks and valleys of adjacent filaments are not as aligned as they were in the overfed web. Preferably, the bloomed filament tow has a pore volume ratio of at least 95%. The tow web can be pulled by hand, or by using an automated device. Alternatively, other methods could be used to produce a filament tow with the desired randomly out-of-phase relationship between filaments, e.g., by stretching an overfed web in other directions than longitudinally, or by using fluid-jet entangling or air entangling to produce the filament tow.

After stretching, the filament tow is cut into lengths 40 (FIG. 3d), each 100 mm long. Cutting can be accomplished using standard equipment, such as that used to cut absorbent materials in conventional tampon manufacture.

Figure 3D:
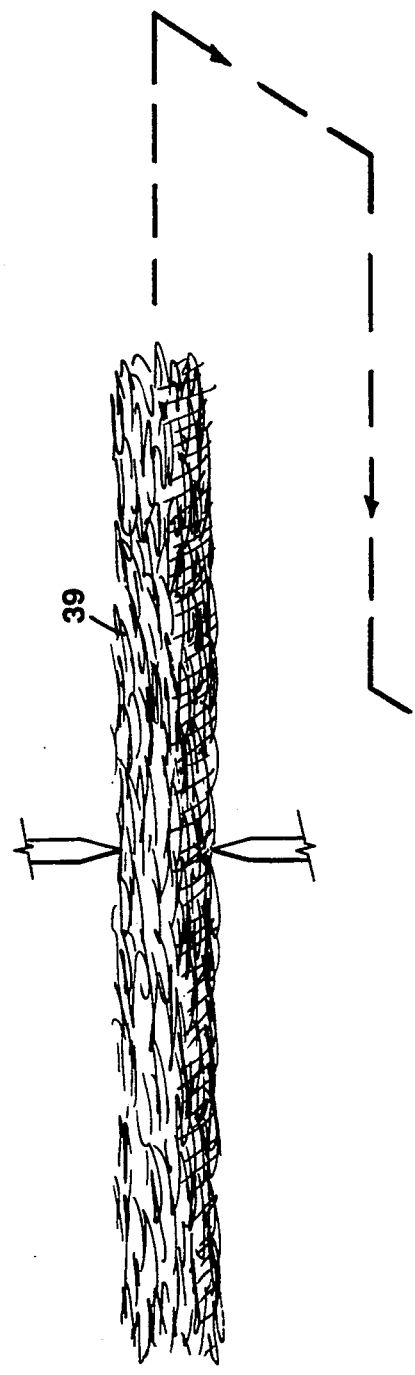
Figure 3D:
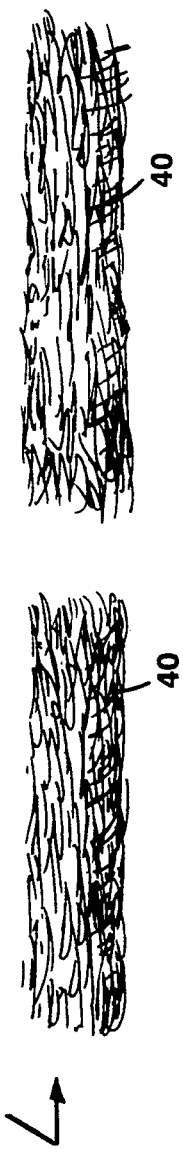
Figure 3E:
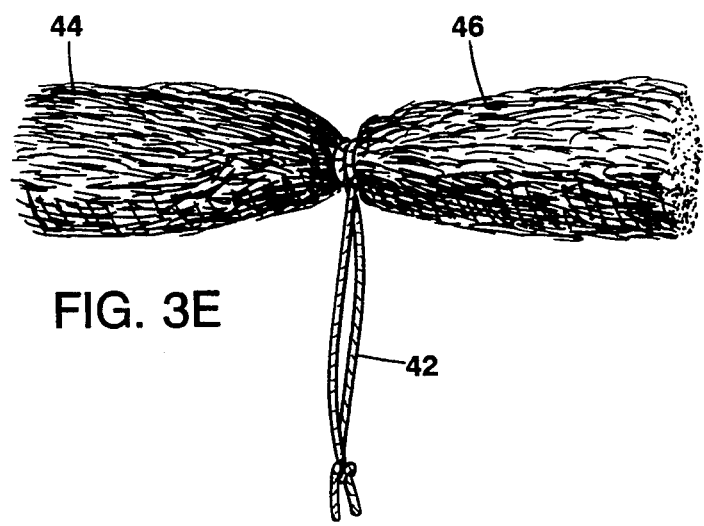
Figure 3F:
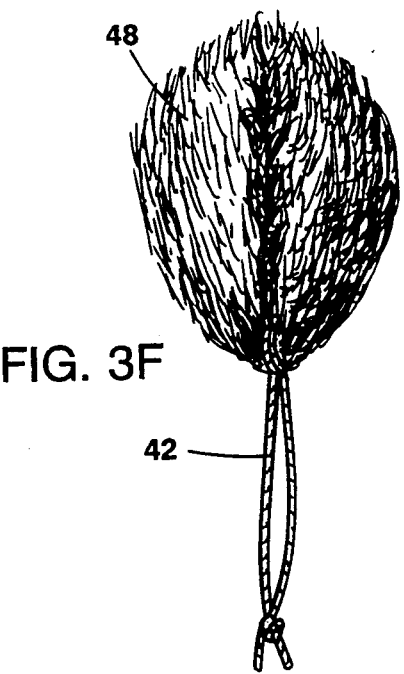

Alternatively, instead of stretching/relaxing the entire tow prior to cutting, the lengths of absorbent material can be stretched/relaxed individually after cutting (i.e., steps FIGS. 3c and 3d can be reversed). However, this is likely to result in a less consistent final product, and cutting the unstretched tow may result in cutting individual filaments in more than one place, causing parts of these filaments to fall off. Also, the material may be cut while it is maintained under tension, and then the individual lengths allowed to relax before further processing.

After the tow has been stretched and cut to length, a withdrawal cord 42 is attached to each length. Preferably, the cord 42 is attached at approximately the midpoint M of the length (FIG. 3e), and is tied relatively tightly around the absorbent material, causing the tied area to be densified in the finished tampon. Optionally, prior to attachment of the withdrawal cord the length of material can be rolled or folded longitudinally (not shown).

The two ends 44, 46 of the length are then folded together (FIG. 3f) to form the pledget 48.

Figure 3G:
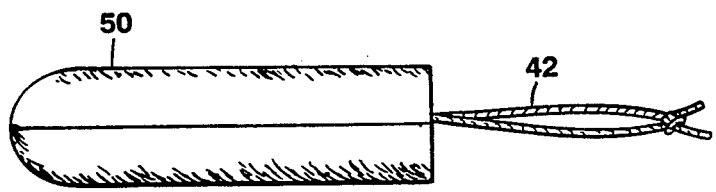

Finally, pledget 48 is radially compressed, to form tampon 50 (FIG. 3g). The pledget is compressed to an extent such that the compressed tampon does not expand significantly during storage under ambient conditions. For example, it is preferred that the tampon expand less than 65% after 48 hours at room temperature, atmospheric pressure, and 50% relative humidity. The longitudinal stretching force used to bloom the web is high enough to break apart the filament relationships in the overfed web, but not so high as to exceed the elastic limit of the crimp (and thus lose the crimp set in the filaments). It is preferred that the compressed pledget have a bulk density of at least 0.05 g/cc, more preferably 0.1 to 0.6 g/cc, and most preferably 0.2 to 0.4 g/cc.

Other embodiments are within the claims. For example, as mentioned above, other filaments may be used, provided they are sufficiently hydrophilic and are able to take on a substantially permanently crimped configuration. The pledget may have shapes other than those shown in FIGS. 1 and 2, and the withdrawal cord may be attached in any suitable manner. Microcrimped filaments may also be used.

We claim:

1. A tampon, shaped for insertion into a body cavity, comprising a compressed pledget, the pledget comprising, prior to compression:
   a portion of absorbent material having a predetermined length, derived from a filament tow and
   a withdrawal cord attached to the filament tow,
   the filament tow comprising a bundle of continuous substantially hydrophilic filaments, each of a major portion of said filaments having a length which is at least substantially equal to said predetermined length,
   the filaments having a substantially permanently crimped configuration, and
   each of a major portion of said filaments having a sinuous configuration that is out-of-phase with respect to that of neighboring filaments.

2. The tampon of claim 1 wherein the uncompressed pledget has a pore volume ratio of at least 95%.

3. The tampon of claim 1 wherein the compressed pledget has a pore volume ratio so that it is in the range of 60 to 95%.

4. The tampon of claim 3 wherein the pore volume ratio is in the range of 70 to 90%.

5. The tampon of claim 4 wherein the pore volume ratio is in the range of 80 to 85%.

6. The tampon of claim 1 wherein the withdrawal cord is attached transversely across the length of absorbent material.

7. The tampon of claim 6 wherein the withdrawal cord is attached at approximately the midpoint of the length of absorbent material.

8. The tampon of claim 7 wherein the length of absorbent material is folded about the midpoint to form the pledget.

9. The tampon of claim 7 wherein the length of absorbent material is fluffed about the midpoint to form the pledget.

10. The tampon of claim 1 wherein the absorbent material comprises cellulosic filaments.

11. The tampon of claim 10 wherein the filaments are viscose.

12. The tampon of claim 1 wherein the filaments are viscose rayon containing carboxyl methyl cellulose (CMC) in amount 4% to 30% by weight.

13. The tampon of claim 1 wherein the filaments are super-inflated rayon.

14. The tampon of claim 1 wherein the filaments have a circular or multi-lobal cross-section.

15. The tampon of claim 14 wherein the filaments have a tri-lobal cross-section.

16. The tampon of claim 1 wherein the crimped configuration is set by means other than heat or mechanical crimping.

17. A tampon of claim 16 wherein the crimped configuration is imparted to the filaments during regeneration of the viscose.

18. The tampon of claim 17 wherein the crimp is imparted by overfeeding the filaments to form a web.

19. The tampon of claim 18 wherein the filaments are overfed into a spreader box under a liquid during regeneration and held in this configuration during further regeneration.

20. The tampon of claim 18 or 19 wherein the blooming of the filaments is achieved by mechanically pulling apart the overfed web.

21. The tampon of claim 20 wherein the mechanical pulling apart consists of pulling primarily along the longitudinal dimension of the web, and then allowing the material to relax.

22. The tampon of claim 21 wherein the pulling does not exceed the elastic limit of the crimp.

23. The tampon of claim 1 wherein the filaments have a water imbibition value of at least 40%.

24. The tampon of claim 1 wherein the filaments contain at least two hydroxyl groups per monomer.

25. The tampon of claim 24 wherein the filaments contain at least three hydroxyl groups per monomer.

26. The tampon of claim 1 wherein the crimp undergoes substantial recovery after extension to but not beyond the elastic limit of the crimp of the individual filaments.

27. The tampon of claim 1 wherein the pledget is compressed sufficiently to prevent it from expanding more than 65% of its initial compressed volume over 48 hours at 50% relative humidity.

28. A tampon, shaped for insertion into a body cavity, comprising a compressed pledget, the pledget comprising, prior to compression:
   a length of absorbent material and
   a withdrawal cord attached to the length of material,
   the length of absorbent material derived from a tow of viscose filaments,
   the filaments having a substantially permanently crimped configuration, each of a major portion of said filaments having a sinuous configuration that is out of phase with respect to that of neighboring filaments, and
   the crimped configuration being imparted by overfeeding the filaments under a liquid during regeneration of the viscose so that the filaments are held in a crimped configuration during regeneration, thereby imparting the permanently crimped configuration;
   the out of phase relationship being imparted by blooming the overfed web.

29. The tampon of claim 28, wherein, prior to blooming, the web is washed and dried.

30. The tampon of claim 29 wherein the web is bleached and finished.

31. The tampon of claim 28 wherein the pledget, prior to compression, has a pore volume ratio of at least 95%.

32. The tampon of claim 28 wherein the degree of overfeed is at least 2:1.

33. The tampon of claim 32 wherein the degree of overfeed is from about 5:1 to 40:1.

34. The tampon of claim 33 wherein the degree of overfeed is from about 15:1 to 25:1.

* * * * *